(12) United States Patent
Taouji et al.

(10) Patent No.: US 8,052,978 B2
(45) Date of Patent: Nov. 8, 2011

(54) VACCINE COMPOSITION AGAINST RHODOCOCCUS EQUI

(75) Inventors: Saïd Taouji, Villenave d'Ornon (FR); Julien Cauchard, Caen (FR); Jean Jacques Ballet, Caen (FR)

(73) Assignee: Agence National de Securite Sanitaire de l'Alimentation, de l'Environnement Et du Travail, Maisons-Alfort (FR)

( * ) Notice: Subject to any disclaimer, the term of this patent is extended or adjusted under 35 U.S.C. 154(b) by 811 days.

(21) Appl. No.: 11/572,293

(22) PCT Filed: Jul. 12, 2005

(86) PCT No.: PCT/FR2005/001793
§ 371 (c)(1),
(2), (4) Date: Jan. 18, 2007

(87) PCT Pub. No.: WO2006/021643
PCT Pub. Date: Mar. 2, 2006

(65) Prior Publication Data
US 2008/0008726 A1  Jan. 10, 2008

(30) Foreign Application Priority Data
Jul. 22, 2004 (FR) ..................... 04 08136

(51) Int. Cl.
*A61K 39/00* (2006.01)
*A61P 43/00* (2006.01)
*C12P 1/04* (2006.01)

(52) U.S. Cl. .................... 424/234.1; 435/170
(58) Field of Classification Search .................... None
See application file for complete search history.

(56) References Cited

U.S. PATENT DOCUMENTS

| 4,803,070 A | 2/1989 | Cantrell et al. | |
| 6,579,524 B1 * | 6/2003 | Corradin et al. | 424/191.1 |
| 2002/0058040 A1 * | 5/2002 | Grimes et al. | 424/185.1 |

FOREIGN PATENT DOCUMENTS

| CA | 2125426 A1 | 12/1995 |
| WO | WO 90/14837 A1 | 12/1990 |
| WO | WO 94/15636 A1 | 7/1994 |
| WO | WO 98/41188 A2 | 9/1998 |
| WO | WO 99/30737 A1 | 6/1999 |
| WO | WO 99/56776 A2 | 11/1999 |
| WO | WO 00/25812 A2 | 5/2000 |
| WO | WO 00/71077 A2 | 11/2000 |
| WO | WO 00/71154 A2 | 11/2000 |
| WO | WO 02/096386 A1 | 12/2002 |
| WO | WO 03/087021 A2 | 10/2003 |

OTHER PUBLICATIONS

ATCC33701 information from www.atcc.org, pp. 1-2. Accessed May 14, 2009.*
ATCC6939 information from www.atcc.org, pp. 1-2. Accessed May 14, 2009.*
*Rhodococcus equi* information from http://emedicine.medscape.com/article/235466-overview, pp. 1-5. Accessed May 14, 2009.*
Skolnick J, Fetrow JS, "From genes to protein structure and function: novel applications of computational approaches in the genomic era," Trends in Biotech., 2000, 18(1): 34-39.*
Becu et al., "Immunopropylaxis of *Rhodococcus equi* pneumonia in foals," Veterinary Microbiology, 1997, 56, 193-204.
Benoit et al., "H2O2, Which Causes Macrophage-Related Stress, Triggers Induction of Expression of Virulence-Associated Plasmid Determinants in *Rhodococcus equi*," Infection and Immunity, Jul. 2002, 70(7), 3768-3776.
Benoit et al., "Introduction of *vap* genes encoded by the virulence plasmid of *Rhodococcus equi* during acid tolerance response," Res. Microbiol., 2001, 152, 439-449.
Higuchi et al., "Clinical evaluation of the serodiagnostic value of enzyme-likned immunosorbent assay for *Rhodococcus equi* infection in foals," Equine Veterinary Journal, 1997, 29(4), 274-278.
Kossovsky et al., "Surface-Modified Diamond Nanoparticles as Antigen Delivery Vehicles," Bioconjugate Chemistry, Sep./Oct. 1995, 6(5), 507-511.
Mueller et al., "Solid lipid nanoparticles (SLN) for controlled drug delivery—a review of the state of the art," European Journal of Pharmaceutics and Biopharmaceutics, 2000, 50, 161-177.
Prescott et al., "Use of *Rhodococcus equi* virulence-associated protein for immunization of foals against *R equi* pneumonia," Am. J. Vet. Res., Apr. 1997, 58(4), 356-359.
Takai et al., "Immunoglobulin and Specific Antibody Responses to *Rhodococcus* (*Corynebacterium*) *equi* Infection in Foals as Measured by Enzyme-Linked Immunosorbent Assay," J. Clin. Microbiology, May 1986, 23(5), 943-947.
Tan et al., "Molecular Characterization of a Lipid-modified Virulence-associated Protein of *Rhodococcus equi* and its Potential in Protective Immunity," Can. J. Vet. Res., 1995, 59, 51-59.

(Continued)

*Primary Examiner* — Julie Ha
(74) *Attorney, Agent, or Firm* — Foley & Lardner LLP (57) ABSTRACT

A method for preparing a soluble antigenic extract from *Rhodococcus equi* is disclosed. The method includes a step of solubilizing membranes of said bacteria by contacting said bacteria with an extraction solution containing a nonionic detergent of sorbitan polyethylene fatty acid ester type. Also disclosed is a soluble antigenic extract obtainable by said preparation method, said extract including membrane antigens of *Rhodococcus equi* dissolved in the extraction solution. Finally, a composition including the soluble antigenic extract as a medicine is disclosed, including preferably a nanoparticulate or oil-in-water emulsion type adjuvant, and the use of the soluble antigenic extract for preparing a pharmaceutical composition for preventing or treating a *Rhodococcus equi*-induced infection in an animal.

28 Claims, 4 Drawing Sheets

OTHER PUBLICATIONS

Taouji et al., "Serum and mucosal antibodies of infected foals recognized two distince epitopes of VapA of *Rhodococcus equi*" FEMS Immunology and Medical Microbiology, 2002, 34, 299-306.

Taouji et al., "Immunogenecity of synthetic peptides representing linear B-cell epitopes of VapA of *Rhodococcus equi*," Vaccine, 2004, 22, 1114-1123.

Vanniasinkam et al., "B-Cell Epitope Mapping of the VapA Protein of *Rhodococcus equi*: Implications for Early Detection of *R. equi* Disease in Foals," J. Clin. Microbiology, Apr. 2001, 39(4), 1633-1637.

Varga et al., "Prevention of *Rhodococcus equi* pneumonia of foals using two different inactivated vaccines," Veterinary Microbiology, 1997, 56, 205-212.

Verschoor et al., "Comparison of Immunity Generated by Nucleic Acid-, MF59-, and ISCOM-Formulated Human Immunodeficiency Virus Type 1 Vaccines in Rhesus Macaques: Evidence for Viral Clearance," J. Virology, Apr. 1999, 73(4), 3292-3300.

Cauchard et al., "Foal IgG and opsonizing anti-*Rhodococcus equi* antibodies after immunization of pregnant mares with a protective VapA candidate vaccine," *Veterinary Microbiology*, vol. 104, pp. 73-81, 2004.

* cited by examiner

VACCINE COMPOSITION AGAINST *RHODOCOCCUS EQUI*

CROSS REFERENCE TO RELATED APPLICATIONS

This application is a National Stage application of PCT/FR2005/001793, filed Jul. 12, 2005, which claims priority from French patent application FR 0408136, filed Jul. 22, 2004.

The subject-matter of the invention is a method for preparing a soluble antigenic extract obtained from *Rhodococcus equi*, comprising a step to solubilize the membranes of said bacteria by contacting these bacteria with an extraction solution containing a nonionic detergent of polyoxyethylene sorbitan fatty acid ester type. A further subject of the invention is a soluble antigenic extract able to be obtained using the preparation method, said extract containing membrane antigens of *Rhodococcus equi* in solution in the extraction solution. A final subject of the invention is a composition comprising the soluble antigenic extract as medicinal product, preferably containing an adjuvant of nanoparticulate or oil-in-water emulsion type, and the use of the soluble antigenic extract to prepare a pharmaceutical composition intended to prevent or treat a rhodococcosis induced by *Rhodococcus equi* in mammalians.

*Rhodococcus equi* (or *R. equi*) is the cause of pyogranulomatous bronchial pneumonias in foals, or other more rare clinical forms (digestive, osteoarticular). The morbidity rate varies from 5% to 17% in the different breeding regions of the world, and the case-fatality rate is 40 to 80%. In Normandy, infections with *Rhodococcus equi* represent approximately 10% of the causes of mortality in foals aged 24 hours to 6 months, with annual variations related to weather conditions (15% in 1988) and represent 70% of bronchial pneumonia cases in animals aged 1 to 6 months.

At the current time, no efficient medical prophylactic means are available. The bacterium is present in the ground of paddocks and pasture-land, and transmission is especially by inhaling contaminated dust from the environment. The disease develops insidiously and only shows clinical signs when the pulmonary lesions are already much advanced, which means that adapted antibiotic treatments (combination of erythromycin-rifampicin) are often applied too late to save the foals. In addition, these antibiotic treatments are costly.

The *Rhodococcus equi* bacterium is a veritable economic blight due to the mortality it causes, but also on account of its consequences for a horse's career and the high cost of treatment. The insidious nature of the disease and the onset of resistant strains means that prevention through the development of an efficient vaccine is a priority in the fight against the pathology.

It is especially carried in the intestines of horses, in particular the intestines of foals in whom insufficient development of anaerobic flora promotes its multiplication. Some authors even consider that *Rhodococcus equi* is a usual host of the digestive tract in Equidae. The germ survives in the ground and can multiply in excrements. This contamination of the outside environment appears to be proportional to Equidae density, and it is very high on stud farms which have been breeding horses for numerous years.

Infections with *Rhodococcus equi* have been described in other animal species: in bovines and porcines *Rhodococcus equi* is chiefly isolated from normal lymph nodes or from lymph nodes with lesions reminiscent of tuberculosis. In slaughterhouses the existence of these forms of adenitis leads to confusion with tuberculosis. In bovines, *Rhodococcus equi* is also responsible for pyometra and pneumonia. In piglets, the germ can be the cause of the formation of abscesses in the oral cavity leading to anorexia. In goats, the formation of pulmonary, spleen and liver abscesses are noted, possibly being attributed to infections with *Corynebacterium pseudotuberculosis*. The formation of abscesses can be accompanied by the development of spinal osteomyelitis. In sheep, some cases of pneumonia, abortions and neonatal mortality have been described. In cats, *Rhodococcus equi* causes adenitis of the anterior mediastinal lymph nodes and of the mesenteric lymph nodes, subcutaneous abscesses and wound infections. Cases of human infection with *Rhodococcus equi* have even been described. Most often this bacterium is isolated in immunodepressed patients (HIV virus infections, immunosuppressive treatments.).

*Rhodococcus equi* bacteria belong to the genus *Rhodococcus*, member of the class Actinobacteria, sub-class Actinobacteridae, order Actinomycetales, sub-order Corynebacterineae, the Nocardiaceae family. The term Corynebacterium equi is sometimes also used to designate *Rhodococcus equi* bacteria.

*Rhodococcus equi* is a Gram-positive, facultative intracellular bacterium, inhibiting phagosome-lysosome fusion and able to survive and multiply in phagocyte cells. Its virulence factors are not fully known, but they appear to be related to the capsule, to "equi factor" synthesis, to mycolic acids, to proteins of 15-17 kDa molecular weight, and to a protein of 20 kDa.

More particularly, the surface proteins of 15 to 17 kDa (or Vap proteins for <<virulence-associated protein>>) are encoded by vap genes carried by plasmids of 85 to 90 kb. Analysis of the restriction fragments allows recognition of at least 10 separate plasmids whose distribution is related to the geographical origin of the strains. In France, the virulent strains have a type I plasmid of 85 kb, or a type I plasmid of 87 kb, or a type II plasmid of 85 kb which has only been found in French strains. These plasmids are only present in the virulent strains, and plasmid-cured strains survive less longer in the phagocytes and are less pathogenic for mice or equidae. The 7 identified vap genes (vapA, vapC, vapD, vapE, vapF, vapG and vapH) are positioned on an island of pathogenicity and encode surface proteins essential for survival in the macrophages, expressed at acid pH and at 37° C. but not at 30° C. The vapA gene sequence appears to be highly conserved, to such an extent that a PCR test amplifying this gene allows diagnosis of the virulent strains. In man, the strains isolated from immunodepressed patients do not all have said plasmid, which contrasts which the strains isolated from sick foals which all contain a plasmid carrying vap genes. It is therefore probable that an immunodepressed state is able to allow even scarcely virulent strains to persist.

At the current time, no commercial vaccine is available in the world to prevent the development of the disease. Hyperimmune plasmas are marketed abroad (Great Britain, United States) but do not have marketing authorization in France. In addition, their efficacy is disputed. French breeders sometimes have recourse to autovaccines produced from local bacterial strains. This situation largely justifies the advantage which would be brought by the commercial development of a vaccine, which could be given to gravid mares for example.

Prescott et al (Am J Vet Res. April 1997; 58(4):356-9) used as antigen a fraction high in VapA proteins. Vaccination prompts the production of G immunoglobulins (IgGs) having opsonizing properties so that the plasma of vaccinated animals can protect foals against experimental infection. However, the vaccination of mothers followed by vaccination of foals does not lead to any protection, and could even increase the seriousness of infections.

The results obtained by Becú et al (Vet microbial. Jun. 16, 1997; 56 (3-4):193-204) using a culture supernatant containing VapA proteins and "equi factor" show that the vaccination of mares protects foals via colostrum antibodies, but that the vaccination of foals is ineffective.

The use of inactivated strains leads to variable results depending on studies. However, for Varga et al (Vet Microbiol. Jun. 16, 1997; 56 (3-4):205-12), the vaccination of foals (2 or 3 injections given between the age of 3 and 7 weeks) does impart protection.

The amino-acid sequence of the VapA protein was published in 1995 (Tan et al, Can J Vet Res. January 1995; 59(1):51-9). Two epitopes of this protein, namely epitope N15Y corresponding to residues 65 to 78 of the mature VapA protein (Vanniasinkam et al, J Clin Microbiol. April 2001; 39(4):1633-7) and V20S corresponding to residues 146 to 160 of the VapA protein (Taouji et al, FEMS Immunol Med Microbiol. Dec. 13, 2002; 34(4):299-306) were designated as having a potential as vaccine against R. equi. In addition, the article published on 26 Feb. 2003 by the National stud farm (Haras Nationaux) ("Immunisation de juments gravides contre des antigènes de R. equi: évaluation de la réponse immunitaire et du transfert passif dans différents élevages normands", Cauchard et al) describes a vaccine composed of antigenic extracts of a virulent strain of R. equi (85Fp$^+$) associated with an adjuvant containing nanoparticles (MONTANIDE IMS3012®). However, this vaccine induces inflammatory reactions at the site of injection.

It is therefore necessary to obtain an improvement, both qualitative and quantitative, in the passive protection afforded to foals by the colostrum. The inventors have been able to develop a new vaccine which induces sustainable immunity against R. equi, which is better tolerated by the animals which received the vaccine with fewer adverse inflammatory reactions, and which is simple to prepare.

This is precisely the object of the present invention.

Therefore according to a first aspect, the subject of the invention is a method for preparing a soluble antigenic extract, obtained from *Rhodococcus equi* bacteria, characterized in that said method comprises the following steps:

a) solubilizing the membranes of the said bacteria by contacting these bacteria with an extraction solution containing a nonionic detergent of polyoxyethylene sorbitan fatty acid ester type, and b) collecting the antigenic extract solubilized at step a).

Data on *Rhodococcus equi*, namely systematics, bacteriological nature, habitat and pathogenic power, pathogenic power in horses, in other animal species or in man, pathogenicity factors, bacteriological and serological diagnosis, sensitivity to antibiotics and prophylaxis are largely described in the dictionary of veterinary bacteriology available on the web site bacterio.cict.fr/bacdico/garde.html.

The R. equi bacteria used in the method of the invention are obtained by culture in a suitable medium and under suitable conditions to implement the invention; preferably, said bacteria are in suspension in the culture medium (<<wet bacteria>>). Without being limited thereto, as example of suitable culture medium mention may be made of the <<Brain Heart Infusion>> (BHI) at a pH of between 5 and 7, preferably between 6 and 7, and more particularly 6.5. The suitable culture conditions are generally room temperature, preferably 37° C., under stirring e.g. 150 rpm for one to several days, preferably for 48 to 72 hours, so that said bacteria are in exponential growth phase.

In the suitable culture medium, said bacteria can be derived from one same strain or from different strains, the bacteria of different strains in this case being in a mixture in the medium.

All strains of R. equi can be used to implement the present invention. As non-limiting examples of R. equi strains the following may be cited: strains ATCC33701, ATCC6939, ATCC2572, and the strain 85F deposited with the national culture collection at Institut Pasteur in France: CNCM (Collection Nationale de Culture de Micro-organismes) located at Institut Pasteur, 25 rue du Docteur Roux, F-75724 PARIS Cedex 15 on 2 Jul. 2004 under number I-3250. All limitations on the deposited materials will be irrevocably removed upon issuance of the patent.

All R. equi strains having a virulence plasmid can be used within the scope of the present invention. Nonetheless, any R. equi strain can also be used in this invention that is plasmid-cured or naturally devoid thereof, to which an expression vector is added containing one or more genes of the pathogenicity island of the natural plasmid.

To recover a soluble antigenic extract from R. equi, the membranes of these bacteria are solubilized by contacting said bacteria, which may be in suspension, in an extraction solution containing a polyoxyethylene sorbitan fatty acid ester which is a nonionic detergent (it is to be noted however that the antigenic extract of R. equi obtained may contain R. equi antigens other than the membrane antigens). This type of nonionic detergent is described in particular in the book: <<Handbook of Pharmaceutical Excipients>>, $2^{nd}$ Edition, <<A joint publication of the American Pharmaceutical Association and the Royal Pharmaceutical Society of Great Britain>>, The Pharmaceutical Press, published by A. WADE and P. J. WELLER, 1994. As examples of polyoxyethylene sorbitan fatty acid esters which can be used at step a) to solubilize the membranes of R. equi bacteria according to the method of the invention, mention may be made without being limited thereto of the following compounds which are commercially available:

polyoxyethylene (20) sorbitan monolaurate, also called polysorbate 20, or TWEEN 20® (AMRESCO, Solon, Ohio);

polyoxyethylene(4) sorbitan monolaurate, also called polysorbate 21, or TWEEN 21®;

polyoxyethylene (20) sorbitan monopalmitate, also called polysorbate 40, or TWEEN 40®;

polyoxyethylene(20) sorbitan monostearate, also called polysorbate 60, or TWEEN 60®;

polyoxyethylene (4) sorbitan monostearate, also called polysorbate 61, or TWEEN 61®;

polyoxyethylene (20) sorbitan tristearate, also called polysorbate 65, or TWEEN 65®;

polyoxyethylene (20) sorbitan monooleate, also called polysorbate 80, or TWEEN 80®;

polyoxyethylene (5) sorbitan monooleate, also called polysorbate 81, or TWEEN 81®;

polyoxyethylene (20) sorbitan trioleate, also called polysorbate 85, or TWEEN 85®; and polyoxyethylene (20) sorbitan monoisostearate, also called polysorbate 120;

The suppliers of these polyoxyethylene sorbitan fatty acid esters are known to those skilled in the art (SIGMA, AMRESCO, etc.).

According to one particular embodiment, the polyoxyethylene sorbitan fatty acid ester is chosen from among polyoxyethylene (20) sorbitan monolaurate, polyoxyethylene (20) sorbitan monopalmitate, polyoxyethylene (20) sorbitan monostearate, and polyoxyethylene (20) sorbitan monooleate.

According to one particularly preferred embodiment, the polyoxyethylene sorbitan fatty acid ester is polyoxyethylene (20) sorbitan monolaurate.

Preferably, the method of preparation according to the present invention is characterized in that said nonionic detergent has a concentration ranging from 0.01% to 5% in said extraction solution.

In particularly preferred manner, the concentration of the nonionic detergent is 0.1% in said extraction solution.

Preferably, at solubilization step a) of the method of preparation according to the present invention, the contacting of the bacteria with the extraction buffer is conducted at a proportion of 1 ml to 20 ml of said buffer per gram of wet bacteria. In best preferred manner, this proportion is 5 ml of said buffer per gram of wet bacteria.

By wet bacteria it is meant to designate bacteria in suspension in a liquid medium.

According to another particular embodiment, the method of preparation according to the present invention is characterized in that the strain of *Rhodococcus equi* bacteria is chosen from among the strains ATCC33701, ATCC6939, ATCC2572 and strain 85F deposited with the CNCM collection on 2 July 2004 under number I-3250.

In particularly preferred manner, the *Rhodococcus equi* bacteria are of strain 85F deposited with the CNCM collection on 2 Jul. 2004 under number I-3250.

According to a further embodiment, the preparation method of the present invention is characterized in that said bacteria are in the form of a bacterial pellet obtained after centrifuging, before step a).

The advantage of this centrifuging step is to remove impurities so that solely bacterial cells are collected. Methods other than centrifuging, well known to those skilled in the art, may also be used for this purpose.

The bacteria in the form of a bacterial residue are obtained by centrifuging under suitable conditions, known to those skilled in the art. Preferably, centrifuging allowing a bacterial residue to be obtained before step a), is conducted at a speed of between 1000 g and 50000 g, preferably 10000 g, for a time of 1 mn to 45 mn, preferably 20 mn, preferably at a temperature ranging from 1° C. to 6° C., preferably 4° C.

Preferably, the bacterial pellet is washed at least once in a suitable washing buffer, before step a).

Persons skilled in the art know which washing buffers are suitable for washing the bacterial pellet. Preferably, Tris acetate buffers are used at an appropriate concentration and pH, e.g. at a concentration of 10 mM or 25 mM, e.g. pH of between 7 and 8, preferably a pH of 7.5. Preferably, said washing buffers are filtered (e.g. using a 0.2 µm filter, . . . ).

In further preferred manner, two successive washings of the bacterial pellet are performed after centrifuging, in a 10 mM Tris acetate buffer of pH 7 to 8, followed by a third washing in a 25 mM Tris acetate buffer of pH 7.5.

Preferably, solubilization at step a) is conducted under stirring at a temperature ranging from 20 to 40° C., in particularly preferred manner at 37° C. for a time of 30 to 150 mn, 90 mn being particularly preferred, and preferably in the presence of microbeads.

Step b) to collect the antigenic extract solubilized at step a) can be conducted using various suitable techniques, such as centrifuging, filtering, chromatography for example.

According to one particular embodiment, the preparation method of the present invention is characterized in that at step b) the product obtained at step a) is centrifuged, and the centrifuging supernatant is collected containing said solubilized antigenic extract.

Centrifuging at Step b) of the product obtained at step a) is performed under suitable conditions known to those skilled in the art. Preferably, this centrifuging is conducted at a speed between 10000 g and 150000 g, preferably 100 000 g, for a time of between 10 mn to 120 mn, preferably for 60 mn at a temperature of between 1 and 6° C., preferably at 4° C.

In further preferred manner, the centrifugation supernatant containing said solubilized antigenic extract is stored at a temperature of between 1 and 6° C., preferably at 4° C.

In particularly preferred manner, the preparation method of the invention is characterized in that the *Rhodococcus equi* bacteria are of the 85F strain deposited with the CNCM collection on 2 Jul. 2004 under number I-3250, and in that the polyoxyethylene sorbitan fatty acid ester is polyoxyethylene (20) sorbitan monolaurate.

According to a second aspect, the subject of the present invention is a method for preparing a soluble antigenic extract obtained from *Rhodococcus equi* bacteria of strain 85F deposited with the CNCM collection on 2 Jul. 2004 under number I-3250, characterized in that said method comprises the following steps:

Obtaining a bacterial pellet by centrifuging said *Rhodococcus equi* bacteria in suspension, at a speed of 10000 g, for 20 mn, preferably at a temperature of 4° C., Conducting two successive washings of the bacterial pellet obtained in a 10 mM Tris acetate buffer of pH 7 to 8, followed by a third washing in 25 mM Tris acetate buffer of pH 7.5, Solubilizing the bacterial membranes of the washed bacterial pellet, by contacting said pellet with an extraction solution containing polyoxyethylene (20) sorbitan monolaurate at a concentration of 0.1% v/v in said extraction solution, the proportion of bacteria/extraction buffer being 5 ml/g wet bacteria, said solubilization being conducted under stirring for 90 mn at a temperature of between 35 and 40° C., preferably in the presence of microbeads, and Centrifuging the product obtained in the preceding step at 100000 g for 1 hour, preferably at 4° C., and collecting the centrifugal supernatant containing said solubilized antigenic extract.

The *R. equi* bacteria used in the method of the invention are obtained by culture in a suitable medium and under suitable conditions for implementing the invention; preferably said bacteria are in suspension in the culture medium. Without being limited thereto, as example of suitable culture medium mention may be made of the BHI medium (Brain Heart Infusion) at a pH of between 5 and 7, preferably between 6 and 7, and in particularly preferred manner of 6.5. The suitable culture conditions are generally room temperature, preferably 37° C., under stirring e.g. 150 rpm, for one to several days, preferably for 12 to 72 hours, so that said bacteria are in exponential growth phase.

During the solubilization step, microbeads can be used to <<break down>> the bacteria. For example glass beads of diameter 150 to 212 µm (SIGMA, Lyon, France) can be used.

According to a third aspect, the subject of the invention is a soluble antigenic extract of *Rhodococcus equi* bacteria which can be obtained using the method of the present invention, characterized in that said extract comprises membrane antigens of *R. equi* in solution in an extraction solution containing a non-ionic detergent of polyoxyethylene sorbitan fatty acid ester type.

According to one particular embodiment, the soluble antigenic extract of *Rhodococcus equi* bacteria according to the invention is obtained using a preparation method according to the present invention.

According to another particular embodiment the soluble antigenic extract of *Rhodococcus equi* bacteria according to the invention, is characterized in that it comprises membrane antigens of *R. equi* in solution in a solution containing a nonionic detergent of polyoxyethylene sorbitan fatty acid ester type.

The membrane antigens of *R. equi* contained in the soluble antigenic extract according to the invention, may be derived from one same strain of *R. equi* or from different *R. equi* strains, the *R. equi* bacteria of different strains in this case being in a mixture in the medium. All *R. equi* strains can be used to implement the present invention. As examples of *R. equi* strains mention may made of the following, without being limited thereto: strains ATCC33701, ATCC6939, ATCC2572 and strain 85F deposited with the CNCM collection on 2 Jul. 2004 under number I-3250, this latter strain being particularly preferred. As mentioned above, all *R. equi* strains having a virulence plasmid can be used within the scope of the present invention. Nonetheless, within the scope of the invention, any *R. equi* strain can be used that is plasmid-cured or naturally devoid thereof, to which an expression vector is added containing one or more genes of the pathogenicity island of the natural plasmid.

Preferably, the soluble antigenic extract of *Rhodococcus equi* bacteria according to the invention is characterized in that the polyoxyethylene sorbitan fatty acid ester is chosen from among polyoxyethylene 20 sorbitan monolaurate, polyoxyethylene 20 sorbitan monopalmitate, polyoxyethylene 20 sorbitan monostearate and polyoxyethylene 20 sorbitan monooleate.

In particularly preferred manner, the soluble antigenic extract of *Rhodococcus equi* bacteria according to the invention is characterized in that the polyoxyethylene sorbitan fatty acid ester is polyoxyethylene 20 sorbitan monolaurate.

Preferably, the soluble antigenic extract of *Rhodococcus equi* bacteria according to the invention is characterized in that said nonionic detergent is in a concentration of between 0.01% to 5%, in said extraction solution.

In particularly preferred manner, the soluble antigenic extract of *Rhodococcus equi* bacteria according to the invention is characterized in that the concentration of the nonionic detergent is 0.1% in said extraction solution.

In best preferred manner, the soluble antigenic extract of the invention is characterized in that the *Rhodococcus equi* bacteria are of the 85F strain deposited with the CNCM collection on 2 Jul. 2004 under number I-3250, and in that the polyoxyethylene sorbitan fatty acid ester is polyoxyethylene 20 sorbitan monolaurate.

According to a fourth aspect, the subject of the invention is a composition comprising the soluble antigenic extract of the present invention, as medicinal product.

Preferably, the composition of the invention as medicinal product further comprises immunity adjuvants; these adjuvants may be of any type known to those skilled in the art provided that, when they are mixed with an efficient quantity of soluble antigenic extract according to the present invention, they allow the antigenic power of the composition to be increased and promote a greater immunity reaction.

Preferably, the composition of the invention is characterized in that it also contains an immunity adjuvant of nanoparticulate type or of oil-in-water emulsion type.

As examples of immunity adjuvants of oil-in-water emulsion type, those adjuvants for vaccines may be cited which give an oil-in-water emulsion and contain a non-mineral oil. Said adjuvants, very well tolerated, are adapted to induce short-term immunity, with humoral mediated response. Preferably, the adjuvant giving an oil-in-water emulsion and containing a non-mineral oil is the adjuvant MONTANIDE ISA 35® (SEPPIC, Paris, France). Generally, this adjuvant MONTANIDE ISA 35® contains a glycerol ester, squalane and anhydromannitol ether octadecanoate, preferably in the following proportions: glycerol ester: 50% squalane: 10% and anhydromannitol ether octadecanoate: 40%.

Mention may also be made, without being limited thereto, of adjuvants of the following oil-in-water type emulsions:
 the adjuvant composition described in the international patent application published on 11 Nov. 1999 under number WO 99/56776 (RIBI ImmunoChem Research Inc) which is a stable oil-in-water emulsion containing a metabolizable oil, one or more surfactants, an antioxidant and a compound to render the emulsion isotonic;
 the submicron oil-in-water emulsions described in the international patent application published on 24 Jun. 1999 under number WO 99/30737 (CHIRON Corp.) relating to vaccine compositions containing firstly biodegradable microparticles with included or adsorbed antigens, and secondly said submicron oil-in-water emulsions;
 the adjuvant composition for vaccines containing a metabolizable oil and an emulsifying agent in which the oil and the emulsifying agent are present in the form of an oil-in-water emulsion (oil droplets with a diameter of approximately 1 micron) such as described in the international patent application published on 13 Dec. 1990 under number WO 90/14837 (CHIRON Corp.), and
 the adjuvant for polysaccharide vaccines comprising an oil-in-water emulsion system containing a light, hydrocarbon non-biodegradable oil, or a biodegradable oil and a detergent, and a detoxified endotoxin such as described in the American patent published on 7 Feb. 1989 under number U.S. Pat. No. 4,803,070 (RIBI ImmunoChem Research Inc.).

As examples of immunity adjuvants of nanoparticulate type, mention may be made of vaccine adjuvants containing liquid nanoparticles associated with an oil-based immunostimulant. Such adjuvants, well tolerated, are based on a new concept grouping together the adjuvant properties of nanoparticles and a novel immunostimulant. Preferably, the additive containing liquid nanoparticles associated with an oil-based immunostimulant is the adjuvant MONTANIDE IMS 301x® (SEPPIC, Paris, France), in particularly preferred manner MONTANIDE IMS 3012®. Generally, this adjuvant MONTANIDE IMS 3012® contains modified corn oil, a saline buffer solution and a preserving agent, preferably in the following proportions: modified corn oil: 10%, saline buffer solution: 89.99%, preserving agent: 0.01%.

Mention may also be made, without being limited thereto, of the following adjuvants of nanoparticulate type:
 small particles (mean diameter: 200 nm) used in particular to administer biologically active agents, described in the international patent application published on 23 Oct. 2003 under number WO 03/087021 (GENESEGUES). Said particles contain a biologically active agent such as an adjuvant, a surfactant, and a polymer soluble in an aqueous solution;
 the solid vaccine adjuvant composition, in the form of powder or granules, containing an injectable solid substrate on which a liquid is able to be absorbed, adsorbed, impregnated or anchored, described in the international patent application published on 5 Dec. 2002 under number WO 02/096386 (SEPPIC);
 vaccine adjuvants of solid, lipid nanoparticulate type described in international patent applications WO 00/71077 (published on 30 Nov. 2000 by PHARMA- SOL), WO 00/71154 (published on 30 Nov. 2000 by PHARMASOL) and in the article by Müller et al. (Eur J Pharm Biopharm July 2000; 50(1):161-77—cf. paragraph 12, page 13);

solid phase adjuvants of metal salt type, in particular aluminium hydroxide gel (ALHYDROGEL) described in the international patent application published on 11 May 2000 under number WO 00/25812 (LEES Andrew). Said adjuvants are described as being used in a method for preparing conjugate vaccines;

the liquid formulation containing a microparticle discontinuous phase in a continuous liquid non-aqueous phase, described in the international patent application published 24 Sep. 1998 under number WO 98/41188 (EASTBRIDGE Limited). The described microparticles contain powdered sugars carrying at least one biomolecular product such as a medicinal product, or other biologically active ingredients such as a protein, an antibody or an enzyme. Said formulation can be used as a vaccine;

diamond nanoparticles with modified surface as administering vehicles for antigens (adjuvants) described in Kossovsky et al, Bioconjug Chem September-October 1995; 6(5); 507-11; and microspherical particles consisting of a continuous matrix of a biodegradable polymer, said matrix particularly containing an immunogen adsorbed on an adjuvant of aluminium salt (aluminium hydroxide, aluminium phosphate . . . ) described in the international patent application published on 21 Jul. 1994 under number WO 94/15636 (CSL Limited).

According to one particular embodiment, the composition of the invention is obtained by mixing the soluble antigenic extract of the invention with the immunity adjuvant, preferably the immunity adjuvant of nanoparticulate type, under gentle stirring for a time of 1 mn to 5 hours, preferably 10 mn, at a temperature of between 1 and 6° C., preferably 4° C. Preferably, before mixing the soluble antigenic extract with the immunity adjuvant, said soluble antigenic extract is previously diluted to a concentration of between 0.5 and 10 mg/ml in the extraction buffer, or any other buffer known to those skilled in the art enabling the structural properties and solubility of proteins to be preserved. Numerous buffers of different composition exist for protein dilution, which may be used in the invention. Further preferably, the soluble antigenic extract is diluted to a concentration of 1 mg/ml. Optionally, the dilution of the soluble antigenic extract is followed by a filtering step or any other method allowing sterile conditions to be maintained.

In particularly preferred manner, the composition of the invention is characterized in that the immunity adjuvant of nanoparticulate type is the MONTANIDE IMS 3012® adjuvant.

In best preferred manner, the composition of the invention contains 50% soluble antigenic extract and 50% nanoparticulate MONTANIDE IMS 3012® adjuvant.

According to another embodiment of the invention, the composition of the present invention is characterized in that the immunity adjuvant of oil-in-water emulsion type is the MONTANIDE ISA 35® adjuvant.

Preferably, the composition of the invention contains 75% soluble antigenic extract and 25% of the oil-in-water emulsion adjuvant MONTANIDE ISA 35®.

According to a fifth aspect, the subject of the invention is the use of a soluble antigenic extract, according to the present invention, to prepare a pharmaceutical composition intended to prevent, or treat an infection with *R. equi* in mammalians. Preferably the mammalian is an equid.

Infections with *R. equi* in mammalians are the cause of various diseases, in particular diseases of the respiratory system. As examples of diseases induced by *R. equi* in foals mention may be made, without being limited thereto, of pyogranulomatous bronchial pneumonia, enterocolitis and multifocal ulcerative typhlitis, often associated with suppurative adenitis of the mesenteric and colic lymph nodes, arthritis, septic osteomyelitis and, more rarely, lymphangitis, myositis and suppurative cellulitis, and subcutaneous abscesses.

In adult horses, the disease is sporadic and translates as pulmonary or colic adenopathies, infected wounds; the bacterium has also been isolated in aborted equine foetuses.

Infections with *Rhodococcus equi* have been described in other mammalian species (bovines, porcines, ovines, caprines, lamas, dogs, cats . . . ) in whom generally the clinical expression of the disease remains unusual. In most cases, the lesions observed are adenopathies, whether suppurative or not; pneumonias are exceptional but have been reported inter alia in sheep, goats and lamas.

On the other hand, in man as in foals, pneumonia is the predominant clinical sign of infections with *Rhodococcus equi*.

Therefore, preferably the use of the present invention is characterized in that infection with *R. equi* induces a disease of the respiratory system, in particular a pneumonia.

In further preferred manner, the use according to the present invention is characterized in that the pharmaceutical composition further comprises an immunity adjuvant.

Further preferably, the immunity adjuvant is of nanoparticulate type or of oil-in-water emulsion type.

In particularly preferred manner, the use according to the present invention is characterized in that the pharmaceutical composition further comprises an immunity adjuvant of nanoparticulate type which is the MONTANIDE IMS 3012® adjuvant.

In best preferred manner, the use according to the present invention is characterized in that the pharmaceutical composition contains 50% of the soluble antigenic extract and 50% of the nanoparticulate adjuvant MONTANIDE IMS 3012®.

According to another embodiment, the use according to the present invention is characterized in that the pharmaceutical composition further comprises an immunity adjuvant of oil-in-water emulsion type which is the adjuvant MONTANIDE ISA 35®.

Preferably, the pharmaceutical composition contains 75% soluble antigenic extract and 25% of the oil-in-water emulsion adjuvant MONTANIDE ISA 35®.

The pharmaceutical composition intended to prevent or treat an infection with *R. equi* can be administered in any appropriate mode to mammalians, preferably Equidae.

Preferably, the use according to the present invention is characterized in that the pharmaceutical composition is administered to said mammalian by intramuscular or subcutaneous route.

According to one particular embodiment, the use according to the present invention is characterized in that the mammalian is chosen from among man, and non-human mammalians, such as bovines, porcines, ovines, caprines, cats. Preferably the mammalian is an equid, a horse in particular.

Preferably, said pharmaceutical composition is administered to foals after birth, preferably 1 to 4 times according to the extent of contamination of the environment.

In particularly preferred manner, the use according to the invention is characterized in that the pharmaceutical composition is intended for the prenatal prevention or treatment of a foal in gestation, said pharmaceutical composition being administered to the gravid mare. Preferably, said pharmaceutical composition is administered 1 to 4 times in relation to the extent of contamination of the environment.

The following keys to the figures and examples are intended to illustrate the invention without limiting its scope in any manner.

EXAMPLES

Example 1

Protocol for Anti-*R. equi* Vaccine Preparation Intended for Gravid Mares (Triton Extraction of Antigens)

The objective of this example is to assess the effect of the immunization of a gravid mare, with a potential vaccine containing VapA associated with a nanoparticulate adjuvant, on specific IgG levels and on serum opsonizing activity transmitted to the foal via the colostrum, and on the onset of *R. equi* pneumonia.
1. Materials and Methods
1.1 Preparation of the Antigens of *Rhodococcus equi*

The purified solution of *R. equi* proteins containing VapA was prepared from the 85F strain and characterized by Western-blot. An injection was prepared containing 1 mg proteins diluted in 0.5 ml Tris acetate buffer, pH 8.5, 2% Triton X-100 (Sigma, St. Quentin Fallavier, France) associated with 0.5 ml of nanoparticulate aqueous adjuvant (IMS 3012, Laboratories SEPPIC, Castres, France). The control animals received the same solution without the proteins. The mares in Group 2 were immunized with a saline solution containing 1.109 fixed bacteria, derived from a culture made with a sample taken from a foal who died of rhodococcosis on one of the stud farms included in the study.
1.2 Animals Forty-eight gravid mares (26 French trotters, 16 English thoroughbreds and 6 ponies of mean age 11 years, range 5 to 17 years) with delivery dates varying between January and July 2002, were included in the study. They were kept on 3 stud farms with enzootic infection of the disease and located in 2 lower Normandy regions (Calvados and Orne). Each mare remained on the same farm for at least 6 months before delivery date and 6 months after foaling.

Seventeen of the 48 brood mares had been immunized 3 times during the previous gestation with whole, inactivated *R. equi* bacteria, and the other horses had never been immunized against *R. equi*. The mares to be immunized for the purposes of the study were divided into 2 groups: Group 1 (24 mares) consisted of mares receiving antigens containing the VapA protein, and Group 2 (8 mares) were mares who received the inactivated whole bacterium (autovaccine). Immunization was made by intramuscular injection into the neck area.

Animals which had received the autovaccine during the previous pregnancy accounted for 9/24 in Group 1 and for 8/8 in Group 2.

The animals in the control group (15 mares) were associated in pairs with those in Group 1, according to delivery dates. The number of foals included in the study was respectively 23, 7 and 13 in Groups 1 and 2 and the control group, there being one case of death at birth due to dystocia in Group 1, and follow-up was discontinued in 3 other cases.
1.3 Immunization Protocol The injections were given at 9, 6 and 3 weeks before the presumed delivery date in Group 1 and the control group, and at 6, 3 and 1 month before the presumed delivery date in Group 2.

After immunization, sera were sampled every week up until delivery, except in 22 brood mares in whom the last blood sample could not be taken due to delivery before term. Samples were taken from the foals at birth, after colostrum transfer (i.e. at 24 hours of life) and at 30 and 45 days of age. Colostrum was sampled at birth. These samples were stored at −20° C. until used for analysis.
1.4 Detection of Anti-*Rhodococcus Equi* IgGs The IgGs were assayed using the ELISA method. 96-well plates (Nalge Nunc, Rochester, N.Y., USA) were coated (1.mu.g/well) with the protein solution containing VapA (cf. 1.1) diluted in PBS at 4.degree. C. overnight, and were then washed three times in PBS, 0.05% v/v TWEEN™ 20 (PBST), and saturated with PBS buffer, 1% BSA at 4.degree. C. overnight, followed by washing three times. The sera were added in triplicate to three dilutions (1/100, 1/1000, 1/50000) and incubated at 37.degree. C. for one hour. After three washings in PBST, the goat anti-horse IgG secondary antibody coupled with peroxidase (1/1600, Bethyl Laboratories, Montgomery, Tex., USA) was incubated one hour at 37.degree. C. After three washings, 100.mu.l TMB (3,3′,5,5′-tetramethylbenzidine) ready for use (Uptima, Interchim, Montlucon, France) were deposited and incubated for 20 min at room temperature. The reaction was stopped with the addition of M H3PO.sub.4. Optical density was read at 415 nm on an automatic spectrometer. The OD value chosen was determined by subtracting the mean OD of the control wells from the mean OD of the experimental sera. Results are expressed in arbitrary units (mean OD for dilution 1/1000, and mean ODs 1/100 and 1/50000 extrapolated to 1/1000). The detection limit was experimentally determined by Western-blot using a serum devoid of antibodies directed against *Rhodococcus equi*.

1.5 Western Blot

The protein solution containing VapA migrated on 12% SDS-PAGE gel. The proteins were transferred onto a nitrocellulose membrane for 90 min at 90 Volts. The membranes were blocked overnight at 4.degree. C. in a TBS-T solution containing 5% BSA, then washed three times with TBS-T (Tris buffer saline, known to persons skilled in the art, associated with TWEEN™). The presence of bands of VapA of 15 Kda was controlled with an anti-VapA rabbit polyclonal antibody (1/2000) prepared by immunization with VapA peptides and developed (1/30000) by goat anti-rabbit IgG secondary antibodies coupled with alkaline phosphatase (Sigma, St. Quentin Fallavier, France). The horse IgGs fixed to the *R. equi* antigens after incubation for 1 hour at 37.degree. C. and three washings, were developed by a secondary antibody (1/5000) of goat anti-horse IgG coupled with alkaline phosphatase (Bethyl, Montlucon, France). After three washings with the TBS-T solution, development was labelled through the addition of 5-bromo-4-chloro-3-indolylphosphate/p-nitro blue tetrazolium (Uptima, Interchim, Montlucon, France). The reaction was stopped through the addition of water.

1.6 Evaluation of Sera Opsonizing Capacities

This entailed counting the number of *R. equi* phagocyted by the polynuclear neutrophils of a clinically healthy adult horse. The freshly taken blood samples, whose red blood cells were lysed (Hybrimax, Sigma) were centrifuged (200 g, 10 min, room temperature). The cell pellet was re-suspended in a Hanks solution. The cells were incubated for 20 min with bacteria derived from an exponential culture of 85F in the presence of the non-decomplemented sera to be tested, then fixed for 5 min in a 0.5% glutaraldehyde solution and stained with Giemsa. The number of bacteria fixed onto 200 polynuclear neutrophils was counted independently by two persons (immersion microscope, 1000×). The controls were devoid of horse serum.

1.7 Clinical Follow-Up

In the mares, local inflammatory reactions at the injection site were noted.

The cases of infection with *R. equi* in foals during the first 6 months of life were also recorded, after confirmation by bacterial isolation from tracheal washing fluid, blood and faeces.

1.8 Statistical Analyses

Whenever possible the results were expressed by a mean value±standard deviation.

The influence of the immunization of mares on colustrum IgG levels, the proportion of mares having anti-VapA antibodies in the different groups, and the comparison between the incidence of the disease in the foals of the 3 groups, were analyzed using ANOVA, $\chi^2$ test and exact Fisher test respectively (Statview 5.0 software).

The effects of immunization of the mares on the kinetics of specific IgGs in the foals were studied using a linear model (GLM procedure, SAS 8.2 software).

Figure 1:
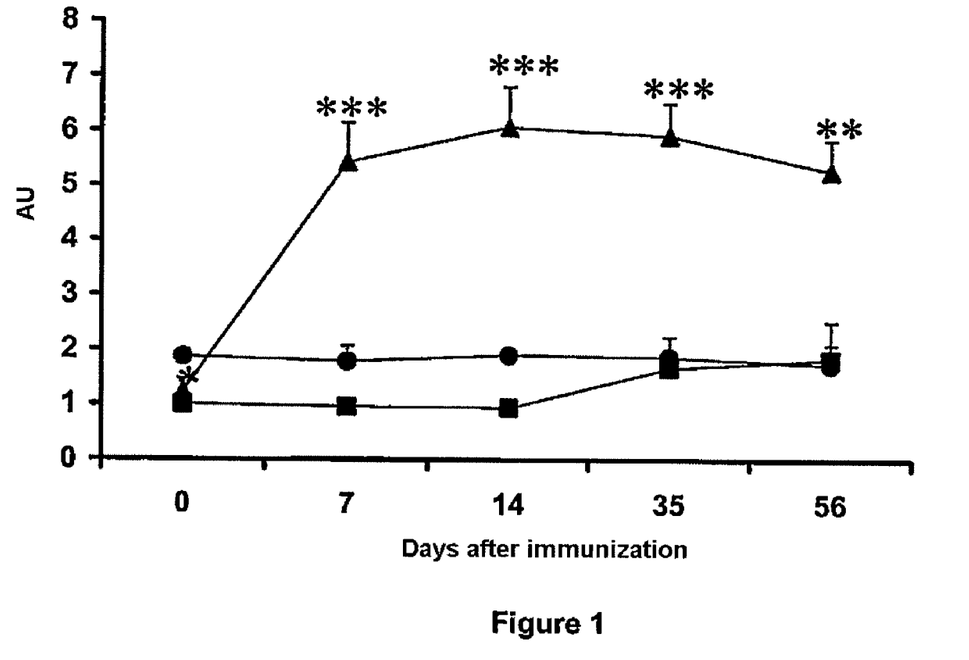
FIG. 1: anti-*R. equi* IgG levels in mares immunized with antigens containing the VapA protein (Group 1), mares immunized with whole, inactivated *R. equi* bacteria (Group 2), and control mares. The IgG levels were determined using the ELISA method. Results are expressed in arbitrary units (AU)+1 standard deviation. Statistical significance of the differences between Groups 1 (▲), 2 (●) and Control (■): *p<0.05, p<0.01, *p<0.001

2. Results 2.1 IgG Levels of Sera Directed against *R. Equi* in Gestational Mares Before and After Immunization The IgG levels determined by ELISA before immunization were significantly higher in Group 2 than in the other two groups (FIG. 1).

In 3 mares of Group 1, significant inflammation was observed at the injection site, which disappeared in 24-48 hours.

After injection of the antigenic preparation containing VapA, the specific IgG levels increased between D0 and D7, then reached a plateau which was maintained up until D56.

On and after the $7^{th}$ day, the antibody levels in Group 1 were significantly higher than in the other two groups.

Figure 2:
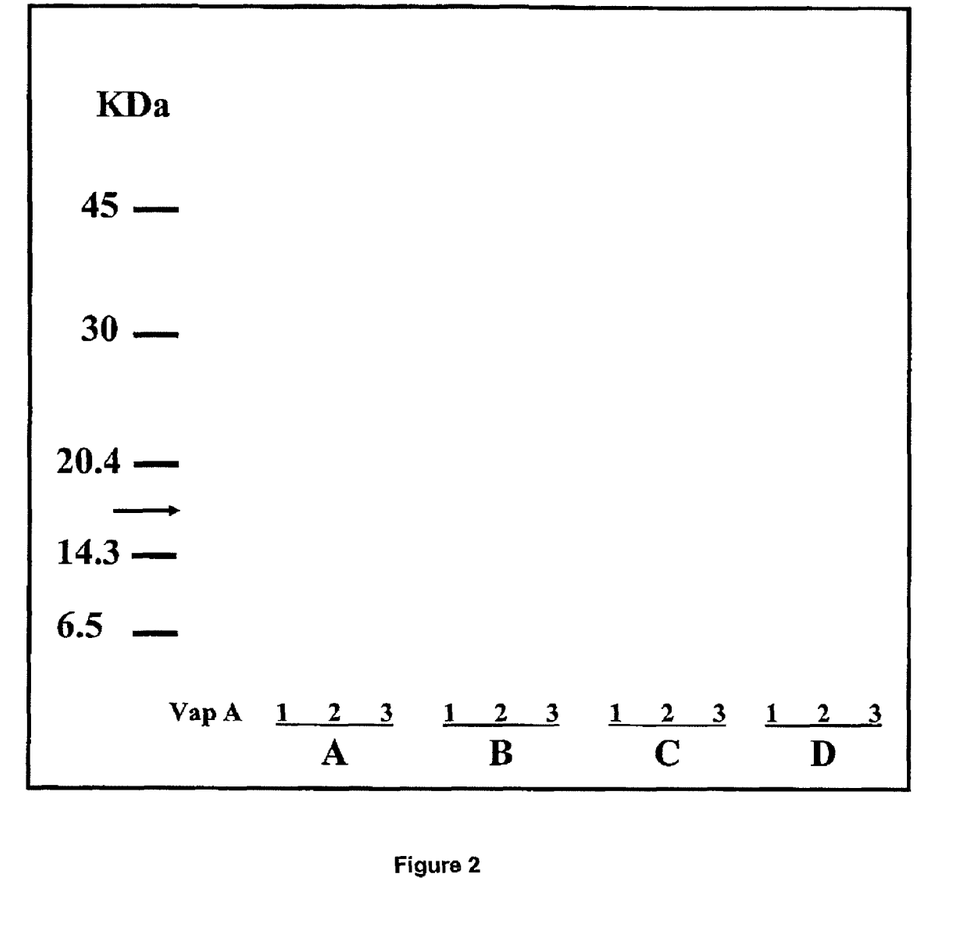
FIG. 2: Western-blot evidencing of anti-VapA serum antibodies. The technique illustrates the binding of the antibodies contained in the tested sera to the 15 KDa band, corresponding to VapA.
  VapA=anti-VapA rabbit polyclonal antibody (arrow)
  A=mare/foal pair (Control group)
  B=mare/foal pair (Group 1)
  C=mare/foal pair, significant transfer of antibodies (Group 2)
  D=mare/foal pair, no transfer of antibodies (Group 2)
  1=sera of mares before immunization
  2=sera of mares 45 days after immunization
  3=sera of foals 30 days after birth.

The presence of anti-VapA IgGs was detected by immunoblots as shown in FIG. 2.

As was predictable, the ratio of animals having specific antibodies before immunization was higher in Group 2 than in Group 1 due to previous immunization (Table 1). All the animals in the control group except one were devoid of detectable anti-VapA antibodies.

Immunization with antigens containing VapA led to the presence of anti-*R. equi* IgGs in 23 mares out of 24 in Group 1, irrespective of their status before immunization, a higher ratio than in Group 2 (p<0.01). Most of the foals in Group 1 showed specific sera antibodies at 30 days after birth, with a higher incidence than in Group 2 (p<0.0001) which differed only slightly from that of the foals in the control group (p=0.04).

TABLE 1

Number of animals having antibodies directed against VapA detected by Western blot, in mares before/after immunization and foals:

|  | Mares D0 | Mares D45* | Foals D30** |
|---|---|---|---|
| Group 1 | 8/24 | 23/24 | 22/23 |
| Group 2 | 6/8 | 7/8 | 4/7 |
| Controls | 1/15 | 2/15 | 4/13 |

Results are expressed as a ratio of the number of animals having *R. equi* antibodies detected by Western blot, over the number of animals in the corresponding group.
*After immunization
**After birth 2.2 Measurement of Colostrum Antibodies The IgGs assayed by ELISA were significantly more abundant in the colustrum of the mares in Group 1 (mean 2.124 AU±0.035) and in Group 2 (mean 1.928±0.160) than in the control mares (mean 1±0.147), (p<0.0001 and p=0.0005 respectively) even though no significant difference was observed between the 2 immunized batches (p>0.05).

2.3 Post-Immunization Kinetics of Anti-*R. Equi* Serum IgGs in Foals

Figure 3:
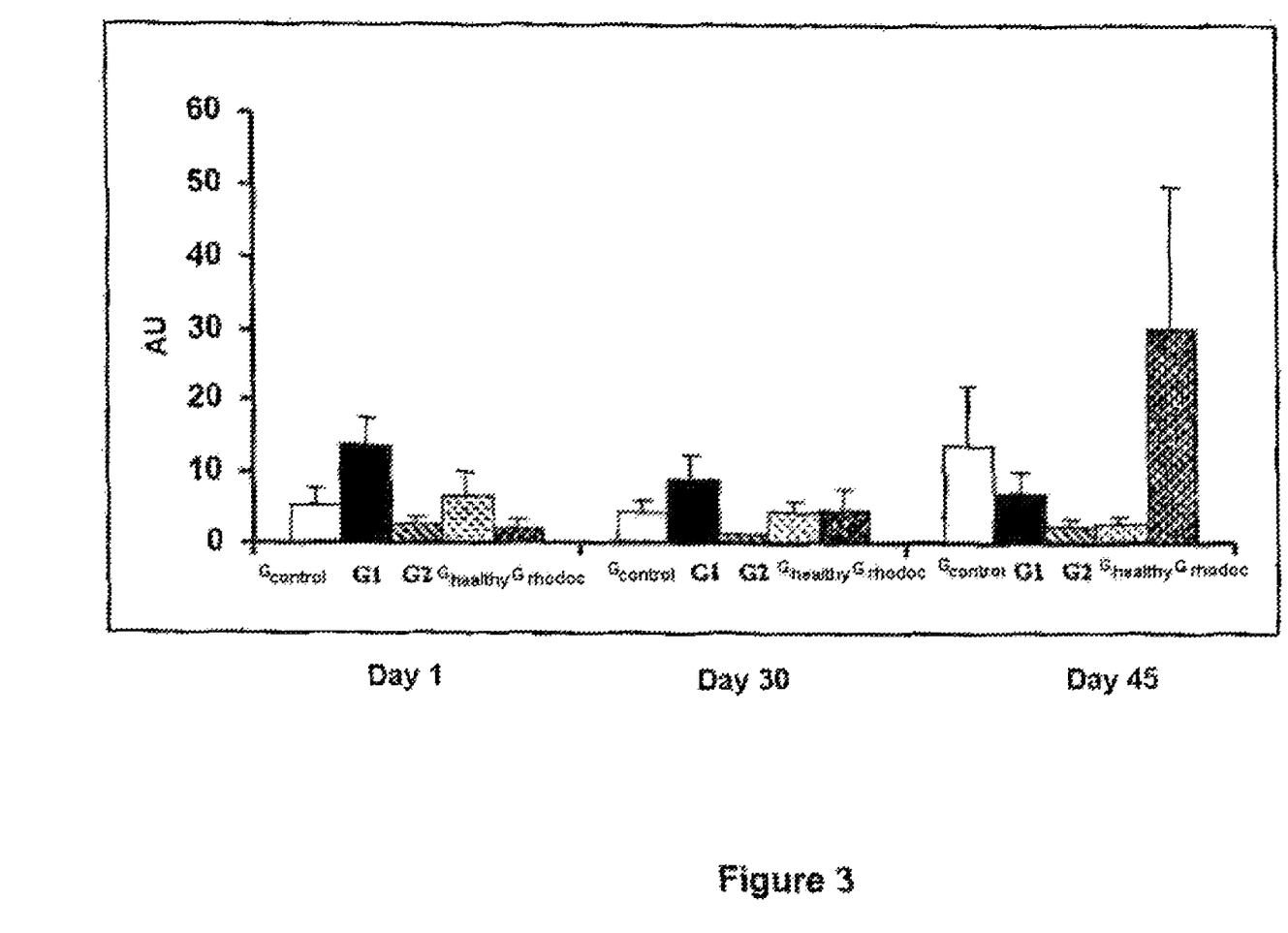
FIG. 3: Kinetics of anti-*R. equi* IgGs in foals born of mares immunized with antigens containing the VapA protein (Group 1, <<G1>>), of mares immunized with whole inactivated *R. equi* bacteria (Group 2, <<G2>>) and of control mares (Control group <<$G_{control}$>>, healthy foals <<$G_{healthy}$>>, foals suffering from rhodococcosis (<<$G_{rhodoc}$>>). Results are expressed in arbitrary units (AU)+1 standard deviation as per the number of days after birth. Statistical significance of differences: *p<5%, p<1%, *p<1%.

The results are detailed in FIG. 3. At birth, anti-*R. equi* serum IgGs detectable by ELISA were not evidenced in any of the foals (newborns).

After colostrum transfer, the 24-hour foals showed anti-*R. equi* antibody levels close to those of their mother (p>0.05; data item not shown). The foals in Group 1 showed higher antibody levels than in Group 2 (p<0.05) which did not differ from those in the control group (p>0.05). The mean antibody levels in Group 1 declined progressively between D1 and D45, remaining higher however than those of the control group at birth, while the values in Group 2 remained stable. The mean antibody level increased at D45 in the control group since 4 foals developed confirmed *R. equi* pneumonia. However, no significant difference with initial values was observed in this group, excluding the foals suffering from pneumonia (p>0.05).

2.4 The Antigenic Preparation Containing the VapA Protein and not the Preparation Consisting of Whole *R. Equi* Bacteria, Significantly Increases Serum Opsonizing Activity in Mares and Foals.

Figure 4:
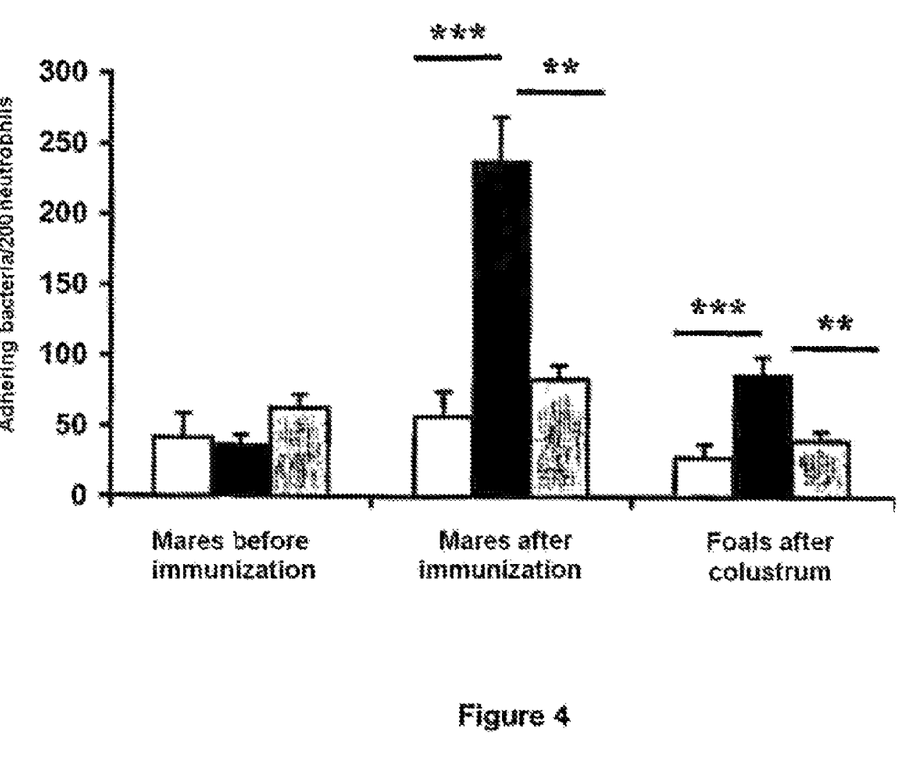
FIG. 4: Opsonization of *R. equi* by the polynuclear neutrophils of mares and foals: controls (☐) Group 2 (▨) and Group 1 (■). Results are expressed as the number of adhering bacteria per 200 polynuclear neutrophils. The sera were tested before the first immunization (Day 0) and after the second immunization (Day 45) for the mares, 30 days after birth for the foals. Statistical significance of the differences: *p<5%, p<1%, *p<1%

On the 45$^{th}$ day after immunization, the serum opsonizing activity was higher in the brood mares of Group 1 (mean number of adhering bacteria per 200 polynuclear neutrophils: 238.6±30.6, FIG. 4) than in Group 2 and the control group (respectively p<0.001 and p<0.01); these two latter groups not showing any difference for this criterion (p>0.05). This activity was transmitted to the foals; the foals in Group 1 showed a mean number of adhering bacteria per 200 polynuclear neutrophils (91.48±11) that was higher than for the foals in Group 2 and the control group (respectively p<0.01 and p<0.001) (FIG. 4).

2.5 Onset of Pneumonia with *R. Equi* in Control Foals and Foals of Immunized Mares.

Four of the 15 foals in the control group showed confirmed pneumonia with *R. equi*, and none of the foals in the two other groups, which his highly suggestive of a protective effect by the immunization (p=0.02).

Example 2

Protocol for Anti-*R. Equi* Vaccine Preparation for Gravid Mares (TWEEN™ Extraction of Antigens)

Bacterial strain: *Rhodococcus equi* 85F deposited with the CNCM collection on 2 Jul. 2004 under number I-3250.
Culture media: Brain-Heart Infusion (BHI) pH 6.5.
Culture conditions: 37° C. under stirring (150 rpm) 48-72 hours. End of exponential growth phase (OD=0.7; reading at 600 mn).
Extraction of Antigens:
Extraction buffer: 25 mM Tris acetate pH 8.5, 0.1% TWEEN™ 20.
Washing buffers: 1) 10 mM Tris acetate pH 7-8
2) 25 mM Tris acetate pH 7.5.
All buffers are filtered (0.2 μm) and stored at 4° C.
Protocol:
1. After centrifuging (10000×g, 20 minutes at 4° C.) the bacterial pellet is washed twice in buffer 1 (5 ml/g wet bacteria) then once in buffer 2.
2. The bacterial pellet is suspended in the extraction buffer at 37° C. for 90 minutes under stirring in the presence of glass microbeads (150 to 212 μm) then centrifuged at 100000×g for 1 hour at 4° C.
3. The supernatant S1 is stored (antigens) at 4° C.
Quality Control by Protein Assay and Electrophoresis.
A. Preparation of Vaccine Doses (Intramuscular Injection, 1 ml).
Adjuvant: IMS 3012 (SEPPIC, France).
Antigen: S1 antigenic solution diluted to 1 mg/ml, then filtered (0.22 μm).
The adjuvant and the antigen are mixed (vol:vol) then the mixture is stirred gently for 10 mn at 4° C.
All operations are conducted under sterile conditions.
Quality Control: Bacteriological.

Comparative Example 3

Unexpected Effect of Tween-20 Compared with Triton in the Preparation of the Antigenic Extracts 24 mares immunized with the adjuvant IMS 3012 associated with the antigenic preparation;

16 control mares who received the adjuvant IMS 3012 without the antigenic preparation.

The mares in the two batches received 3 injections (2 if delivery before term).

After the onset of inflammatory reactions, both in the chest and neck region, the possibility was considered that the antigenic preparation could be the cause of these reactions. It was decided to modify the preparation of the antigenic extracts and to replace Triton by Tween-20 as detergent. The results observed are given in the table below:

| Mare Group | N° of mares | Injected doses | N° of reactions with Triton | N° of reactions with Tween-20 |
|---|---|---|---|---|
| Immunized | 24 | 63 (41 Triton/22 Tween-20) | 3 major 4 minor | 0 |
| Controls | 16 | 45 (32 Triton/13 Tween-20) | 0 | 0 |

The invention claimed is:

1. A vaccinal composition comprising a soluble antigenic extract of *Rhodococcus equi* bacteria and an immunity adjuvant, wherein said antigenic extract comprises the *R. equi* membrane antigens selected from the group consisting of the VapA antigen and its epitopes N15Y and V20S in solution in an extraction solution containing a nonionic detergent of polyoxyethylene sorbitan fatty acid ester type.

2. The composition of claim 1, wherein the immunity adjuvant is a nanoparticulate type immunity adjuvant or an oil-in-water emulsion type immunity adjuvant.

3. The composition of claim 2, wherein the immunity adjuvant of nanoparticulate type contains 10% of modified corn oil, 89.99% of saline buffer solution and 0.01% of preserving agent.

4. The composition of claim 3, wherein it contains 50% of the soluble antigenic extract and 50% of said nanoparticulate adjuvant.

5. The composition of claim 2, wherein the immunity adjuvant of oil-in-water emulsion type contains 50% of glycerol ester, 10% of squalane and 40% of anhydromannitol ether octodecanoate.

6. The composition of claim 5, comprising 75% of the soluble antigenic extract and 25% of said oil-in-water emulsion adjuvant.

7. The composition of claim 1, wherein the polyoxyethylene sorbitan fatty acid ester is chosen from among polyoxyethylene 20 sorbitan monolaurate, polyoxyethylene 20 sorbitan monopalmitate, polyoxyethylene 20 sorbitan monostearate and polyoxyethylene 20 sorbitan monooleate.

8. The composition of claim 7, wherein the polyoxyethylene sorbitan fatty acid ester is polyoxyethylene 20 sorbitan monolaurate.

9. The composition of claim 1, wherein said nonionic detergent is at a volume to volume concentration of between 0.01% and 5% (v/v) in said extraction solution.

10. The composition of claim 9, wherein the concentration of the non-ionic detergent is 0.1% v/v in said extraction solution.

11. The composition of claim 1, wherein the strain of the *Rhodococcus equi* bacteria is chosen from among the strains ATCC33701 and strain 85F deposited with the CNCM on 2 Jul. 2004 under number I-3250.

12. The composition of claim 11, wherein the *Rhodococcus equi* bacteria are of the strain 85F deposited with the CNCM on 2 Jul. 2004 under number I-3250.

13. A method of treating a mammal suffering from an *R. equi* infection comprising administering to a mammal in need thereof a pharmaceutical composition comprising a soluble antigen extract composition as defined in claim 1.

14. The method of claim 13, wherein the mammalian is an equid.

15. The method of claim 13, wherein the infection with *R. equi* induces pneumonia.

16. The method of claim 13, wherein the pharmaceutical composition further comprises an immunity adjuvant of nanoparticulate type or of oil-in-water emulsion type.

17. The method of claim 13, wherein the pharmaceutical composition is administered to said mammal via intramuscular or subcutaneous route.

18. The method of claim 13, said pharmaceutical composition being administered to the gravid mare for the prenatal treatment of a foal in gestation.

19. A method for preparing a soluble antigenic extract, obtained from *Rhodococcus equi* bacteria, said method comprising the following steps:
  a) Solubilizing the membranes of said bacteria by contacting these bacteria with an extraction solution containing a nonionic detergent of polyoxyethylene sorbitan fatty acid ester type, and
  b) Collecting the antigenic extract solubilized at step a), wherein the *Rhodococcus equi* bacteria are of strain 85F deposited with the CNCM on 2 Jul. 2004 under number I-3250.

20. The method of claim 19, wherein the polyoxyethylene sorbitan fatty acid ester is chosen from among polyoxyethylene 20 sorbitan monolaurate, polyoxyethylene 20 sorbitan monopalmitate, polyoxyethylene 20 sorbitan monostearate and polyoxyethylene 20 sorbitan monooleate.

21. The method of claim 20, wherein the polyyoxyethylene sorbitan fatty acid ester is polyoxyethylene 20 sorbitan monolaurate.

22. The method of claim 19, wherein said nonionic detergent has a volume to volume concentration of between 0.01% and 5% (v/v) in said extraction solution.

23. The method of claim 22, wherein the concentration of the non-ionic detergent is 0.1% v/v in said extraction solution.

24. The method of claim 19, wherein at the solubilization step a), the contacting of the bacteria with the extraction buffer is performed at a proportion of 5 ml of said buffer per gram of wet bacteria.

25. The method of claim 19, wherein said bacteria are in the form of a bacterial pellet obtained after centrifuging, before step a).

26. The method of claim 25, wherein at least one washing of the bacterial pellet is performed in a suitable washing buffer, before step a).

27. The method of claim 19, wherein at step b) the product obtained at step a) is centrifuged, and the centrifugal supernatant containing said solubilized antigenic extract is collected.

28. A method of preparing a soluble antigenic extract obtained from *Rhodococcus equi* bacteria of strain 85F deposited with the CNCM on 2 Jul. 2004 under number I-3250, wherein said method comprises the following steps:
  Obtaining a bacterial pellet by centrifuging said *Rhodococcus equi* bacteria in suspension at a speed of 10000 g for 20 nm, preferably at a temperature of 4° C.,
  Two successive washings of the bacterial pellet obtained in a 10 mM Tris acetate buffer of pH 7 to 8, followed by a third washing in a 25 mM Tris acetate buffer of pH 7.5,
  Solubilizing the bacterial membranes of the washed bacterial pellet by contacting said pellet with an extraction solution containing polyoxyethylene 20 sorbitan monolaurate at a concentration of 0.1% (v/v) in said extraction solution, the proportion of bacteria/extraction buffer being 5 ml of said buffer per gram of wet bacteria, said solubilization being conducted under stirring for 90 nm at a temperature of between 35 and 40° C., and
  Centrifuging the product obtained at the preceding step at 100000 g for 1 hour, preferably at 4° C., and collecting the centrifugal supernatant containing said solubilized antigenic extract.

* * * * *